United States Patent [19]
Tong

[11] Patent Number: 4,562,110
[45] Date of Patent: Dec. 31, 1985

[54] PROCESS FOR THE PRODUCTION OF ALGINATE FIBRE MATERIAL AND PRODUCTS MADE THEREFROM

[76] Inventor: David P. Tong, 54 Berrington Rd., Nuneaton, Warwickshire, England

[21] Appl. No.: 408,973

[22] Filed: Aug. 17, 1982

[30] Foreign Application Priority Data

Aug. 18, 1981 [GB] United Kingdom ............... 8125178

[51] Int. Cl.⁴ ..................... D01F 9/04; A61F 13/00; A61L 15/00
[52] U.S. Cl. .................................. 428/284; 128/155; 128/156; 264/103; 264/186; 264/213; 428/370; 428/371
[58] Field of Search ............... 106/208; 264/202, 213, 264/186; 128/156, 155; 428/284, 370, 371

[56] References Cited

U.S. PATENT DOCUMENTS

| | | | |
|---|---|---|---|
| 1,225,833 | 5/1917 | Lilley | 128/156 X |
| 1,786,781 | 12/1930 | Shoemaker | 128/155 X |
| 2,371,717 | 3/1945 | Speakman | 264/186 |
| 2,375,650 | 5/1945 | Hegan et al. | 106/208 |
| 2,423,075 | 6/1947 | Hall | 106/208 |
| 2,461,094 | 2/1949 | Taylor | 264/184 |
| 2,521,738 | 9/1950 | McMeekin et al. | 264/202 X |
| 2,541,804 | 2/1951 | Wormell | 264/202 |
| 3,060,501 | 10/1962 | Beal | 264/180 |
| 3,063,454 | 11/1962 | Coates et al. | 128/156 X |
| 3,242,120 | 3/1966 | Steuber | 106/208 |
| 3,545,442 | 12/1970 | Wicker et al. | 128/156 X |
| 3,550,592 | 12/1970 | Bernardin | 128/290 |
| 3,689,620 | 9/1972 | Miyazaki et al. | 264/181 |
| 3,802,980 | 4/1974 | Harmon | 156/181 |
| 3,824,996 | 7/1974 | Carlisle | 128/156 |
| 3,824,997 | 7/1974 | Franklin et al. | 128/156 |
| 3,867,935 | 2/1975 | Eisdorfer et al. | 128/156 |
| 3,882,063 | 5/1975 | Gouw | 264/163 |
| 4,016,236 | 4/1977 | Nagasawa et al. | 264/184 |
| 4,080,163 | 3/1978 | Kawai et al. | 8/115.5 |
| 4,104,115 | 8/1978 | Prouse et al. | 162/100 |
| 4,187,343 | 2/1980 | Akigama et al. | 264/119 |

FOREIGN PATENT DOCUMENTS

| | | | |
|---|---|---|---|
| 453829 | 1/1949 | Canada | 264/202 |
| 2708822 | 9/1977 | Fed. Rep. of Germany | 128/155 |
| 2418821 | 9/1979 | France | 264/184 |
| 567641 | 2/1945 | United Kingdom | 264/202 |
| 568177 | 3/1945 | United Kingdom | 264/202 |
| 571657 | 9/1945 | United Kingdom | 264/202 |
| 624987 | 6/1949 | United Kingdom | 264/202 |
| 653341 | 5/1951 | United Kingdom . | |
| 1394741 | 5/1975 | United Kingdom . | |

OTHER PUBLICATIONS

McDowell, R. H., *Properties of Alginates*, 4th Edition, London, Eng., Alginates Indust., Ltd., ©1977, p. 1.
WO80/02300, 10/30/80, WIPO (Courtaulds Ltd.), Aldred, Fred Crowther et al., 1 Sht. Drwg.; 8 pp.
*Hackh's Chemical Dictionary*, Fourth Edition, Completely Revised and Edited by Julius Grant, New York, McGraw-Hill, ©1972, pp. 25, 536, 550, 551.
*The Condensed Chemical Dictionary*, Tenth Edition, Revised by Gessner G. Hawley, New York, Van Nostrand Reinhold, ©1981, pp. 24, 29, 30, 838, 867, 868.

*Primary Examiner*—Philip Anderson
*Attorney, Agent, or Firm*—Neil F. Markva

[57] ABSTRACT

A process for producing dried alginate fibre material, in which wet spun insoluble alginate fibres are overlaid in a sheet onto a more slowly moving liquid permeable conveyor and are subjected to a dewatering drying operation, includes special treatment to eliminate or reduce bonding of the overlaid fibres at their points of contact or intersection. This is accomplished preferably by passing the dried sheet or web that is produced through successive pairs of rollers driven at different speeds so as to pull the individual fibres longitudinally and break any existing inter-fibre bonds. Also, prior to and during initial drying of the sheet of wet fibres application thereto of external mechanical forces is avoided and alcohol exchange to remove water may be used. The rollers may advantageously produce a stretch-breaking effect. The alginate fibre material produced is particularly suitable for making up medical or surgical dressings and the like.

42 Claims, 1 Drawing Figure

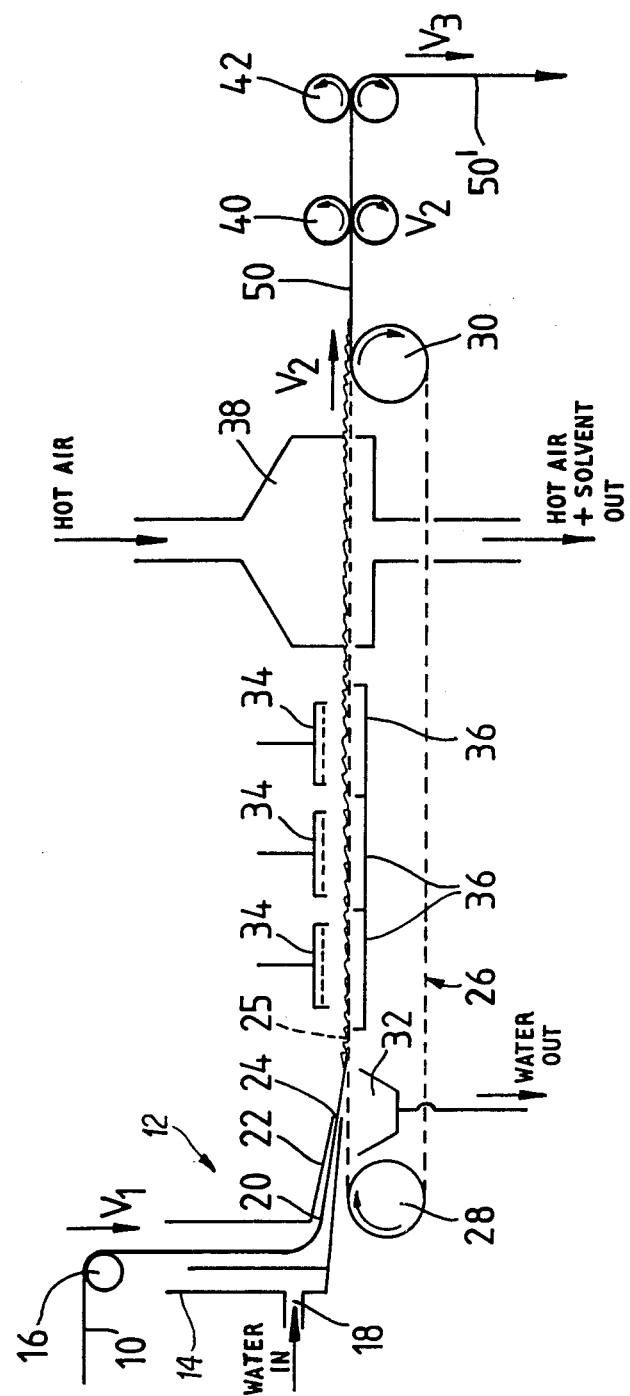

PROCESS FOR THE PRODUCTION OF ALGINATE FIBRE MATERIAL AND PRODUCTS MADE THEREFROM

BACKGROUND OF THE INVENTION

The present invention relates to a process for the production of alginate fibres, particularly dried alginate fibre material, and to products made therefrom; it is especially, although not exclusively, useful for the commercial manufacture and preparation of materials and products, composed of alginate fibres, for use as swabs or dressings and the like suitable for medical, surgical and other purposes.

The extrusion of alignate solutions into coagulating baths or spin baths containing for example aqueous solutions providing calcium ions to form or spin yarns of insoluble alginate salt filaments is a well known process.

It is also well known to prepare and use materials or fabrics composed of alginate fibres, especially calcium and sodium/calcium mixed salt alginate fibres, for surgical and medical purposes, for instance in the form of dressings and the like in connection with which the hemastatic properties of the alginate and, in some cases, solubility in body fluids can be particularly valuable. Such uses are for example described in British Pat. Nos. 653341 and 1394741.

In the past, alginate fabrics for providing surgical and medical dressings and the like have generally been produced from continuous calcium alginate filament yarn by knitting. When the alginate material is required in the more soluble sodium/calcium mixed salt form, which is commonly preferred and is more useful in many cases, the knitted fabric is then treated or "converted" to replace part of the calcium content by the more solubilizing sodium cation.

This conversion of the calcium alginate to the more soluble sodium/calcium alginate mixed salt form is the subject of a number of Patent publications and an excellent summary is given in British Pat. No. 1394741 which sets out the basis for a process which is technically superior to previous methods. In practice, however, the treatment or conversion process performed on the knitted fabric has usually involved handling problems and has been carried out batchwise which is rather inefficient and uneconomic resulting in a costly and wasteful production process.

As will be seen later, the process of the present invention can enable calcium alginate fibres to be wet spun and processed to form a dried alginate fibre material in a continuous series of operations which can include, when required, a step of converting the calcium alginate fibre material into the sodium/calcium mixed salt form. The dried alginate fibre material so formed may then be made up into a tow suitable for swab production or alginate wool or into the form of a non-woven wadding suitable for use as a medical or surgical dressing. The entire process can be performed without handling the material, using simple machinery which is easy to maintain to the standards of cleanliness required of this type of product.

A factor to be considered, however, in the production and processing of alginate fibres is the tendency of such fibres, when wet, to adhere and fuse together on drying. This tendency is of major importance in the drying of wet newly-spun "never-dried" alginate fibres since these are extremely soft and have a very high water content so that, during drying, considerable dewatering takes place and adjacent individual fibres or filaments are caused to adhere to each other by capillary action and become bonded together. This bonding effect can be dramatically increased by any mechanical forces externally applied at the dewatering drying stage.

It may be noted that this tendency for inter-fibre bonding to occur is not so important in drying "re-wetted" alginate fibres, that is, alginate fibres or yarns which have been dried after being initially spun and which have then subsequently been re-wetted. In the latter case, provided a significant degree of fibre bonding has been avoided in first producing and drying the fibres it is found that on subsequent re-wetting considerably less water is taken up by the fibres and during re-drying the tendency for the fibres to adhere and bond together is very much reduced. On the other hand, in any continuous production process which starts with the initial step of wet spinning calcium alginate fibre filaments one is necessarily dealing with "never-dried" alginate fibres which remain wet up to the drying stage at which the tendency to adhere and bond together arises as discussed above.

In the commercial production of continuous dried alginate filament yarns the problem of excessive and undesirable bonding between individual fibre filaments may be overcome by coating the filaments before drying with a substance such as an emulsified oil which prevents the filaments from sticking together. Or, as an alternative remedy, fibre adhesion may be inhibited by exchanging and removing the water with an organic water soluble solvent such as acetone or a lower alcohol at a sufficiently high concentration.

It has been already-dried alginate filament yarns as referred to above which have previously been commonly used for making knitted alginate fabrics in the conventional processes for providing surgical and medical alginate dressings. It has, however, also been proposed in publication document WO 80/02300 of International Patent Application No. PCT/GB80/00066 (Courtaulds Limited) to provide a non-woven alginate fabric for use as an alginate dressing and a process for the production of such non-woven fabric is disclosed therein.

According to the process of WO 80/02300, a tow of stretched and washed spun calcium alginate fibres or filaments is passed in a flow of water through a spreading device, such as a device with a "fish tail" outlet, and the spread band or sheet produced is fed forwards and deposited on a liquid permeable conveyor, such as Fourdrinier wire mesh conveyor, moving at a slower speed so that the fibres are overlaid in a substantially uniform layer or sheet forming a web which is then dried to provide a unitary non-woven alginate fabric. As a result of the overlaying, the fibres become crimped or looped and cross over each other in the web so that a parallel orientation thereof is destroyed; it will be appreciated that this reduces the contact area of the fibres and prevents the formation, in the subsequent dewatering drying operation, of a sheet in which parallel fibres are bonded and fused together along their length. Such a sheet of parallel bonded alginate fibres would be completely unsuitable for medical or surgical alginate dressings.

The advantages resulting from overlaying the fibres as described above suggests that no other special measures need to be taken to counteract bonding together of the fibres. Indeed, on the contrary, the disclosure in WO 80/02300 indicates that some fibre bonding is desirable and particularly emphasizes that although lengthwise bonding is avoided the overlaid fibres in the web produced should still be bonded at their points of contact where they cross over each other; the drying operation in the process described accordingly is carried out in a way which applies mechanical forces and promotes such bonding at intersections, first by applying suction directly to the wet overlaid fibres on the conveyor and then by passing the partially dried web around heated cylinders. Also, a way of further increasing the degree of such inter-bonding by a treatment of the filaments on the conveyor with an aqueous solution of a sodium salt, preferably a sodium salt of an acid which forms on insoluble calcium salt, before completing the drying operation is described. A non-woven alginate fabric is thus produced by the process of WO 80/02300 consisting essentially of a dried web of intersecting alginate fibres or filaments bonded together at their cross-over points to provide a strong unitary structure.

The production of non-woven unitary webs or fabrics directly from tows of continuous synthetic textile filaments is also already known from U.S. Pat. No. 3,802,980 (Harmon) which describes a manufacturing process similar in some ways to that described in WO 80/02300, especially in respect of the use of a fish-tail type spreader to overfeed onto a more slowly moving liquid permeable conveyor a thin sheet or band of filaments or fibres so that the latter become crimped and overlaid in crossing-over or intersecting overlapping relationship in a continuous filament sheet which is then dried to produce the non-woven unitary web required. The fibres or filaments of the web produced are not described as being bonded and it is implied that frictional engagement between overlapping crimped or looped fibre portions of adjacent individual filaments suffices to maintain a unitary structure. This may be so, although it is notable that in the specific examples described the filament sheet on the conveyor is sprayed before final drying with a polyvinyl alcohol solution which is known to act as an adhesive and promote bonding to some extent with many fibres.

In any event, the process of U.S. Pat. No. 3,802,980 is not specifically described as being applied to alginate fibres or filaments but appears to be directed more to synthetic textile filaments such as viscose rayon, nylon, polyesters, acrylics and polyolefins etc., and it can be inferred that the initial tows to which it is expected that the process would be applied would be composed of already dried continuous filaments of these materials. If, on the other hand, the process were to be applied to "never dried" alginate fibres and carried out exactly as described using in particular a suction box to remove water from the freshly laid sheet or web on the conveyor, a high degree of bonding between the fibres or filaments at their cross-over points would inevitably be obtained as in the process of WO 80/02300. This, however, would be quite in accordance with the teaching of the latter and may therefore well be considered to represent a useful advantage.

SUMMARY OF THE INVENTION

The process of the present invention has some features in common with that described in WO 80/02300 but it differs in certain very significant respects and there is a fundamental difference in that it departs completely from the teaching of the latter in regard to endeavoring to produce as an end product a unitary non-woven web or fabric composed of a dried sheet of overlaid alginate fibres or filaments which are bonded together where they intersect and cross over each other. On the contrary, the present invention seeks to provide a process, which can be continuously operable, adapted to produce a unitary dried non-woven web of non-bonded alginate fibres.

Thus, according to the present invention a process for the production of dried alginate fibre material includes the operations of spinning an aqueous solution of a soluble alginate salt into a spin bath containing an aqueous solution of a salt, for example a calcium salt, to provide wet spun fibres of insoluble alginate, forming a sheet of the wet spun insoluble undried alginate fibres in which the individual fibres are separated and disposed in generally parallel relationship, feeding forwards and laying the sheet of undried fibres onto a moving conveyor device which is travelling at a slower speed than said sheet in the feed direction whereby the fibres become overlaid in crossingover intersecting relationship to form a web having a defined width. Then the sheet or web of intersecting overlaid fibres is subjected to a dewatering drying operation. The process includes at least one controlled treatment step which is effective to eliminate or reduce bonding of the overlaid fibres at their points of contact or intersection and to ensure thereby that the dried non-woven web constituting the dried alginate fibre material which is the end product of said process has minimal degree of bonding between the fibres.

It will be appreciated that in the present specification the term "web" is used in a broad sense to include any sheet-like layer or matrix of individual fibres and it does not imply that there is necessarily some significant degree of actual bonding or strong permanent adhesion between the individual fibres thereof.

It has been found that, despite the teaching of WO 80/02300, dried non-woven alginate fibre webs made in accordance with the present invention so as to have but a minimal degree of bonding between the fibres afford a material which, for the purpose of providing products such as surgical or medical dressings and swabs and the like, is in general much superior to that afforded by dried non-woven alginate fibre webs having a high degree of fibre-fibre bonding.

This superiority arises primarily from the fact that the webs made in accordance with the invention with minimal inter-fibre bonding present a significantly softer texture and offer greater scope for various different finishing operations in preparing or making up final materials or products having desired characteristics for surgical or medical use. As will hereinafter be apparent, a range of options is available for further processing these webs of dried alginate fibre material for the purposes required, including making up into comparatively thick multilayer fabrics by cross-laying and introducing a carefully controlled amount of bonding between layers to provide soft non-woven wadding, and forming or gathering into a tow of separate and substantially parallel fibres which can then be staple cut and used to make wadding by air laying or to make alginate wool with a further option of introducing and blending with other different fibres.

Advantageously in some cases, as hereinafter described in accordance with a further aspect of the invention, the fibres of such webs may also be randomly broken by a stretch breaking operation before being made up for example into a cross-laid multilayer fabric for wadding, this stretch breaking yielding material of non-bonded fibres which may be similar to that produced by a textile card.

In contrast with the material obtained by means of the present invention, non-woven alginate fibre webs having a high degree of inter-fibre bonding as produced by the process of WO 80/02300 form a relatively harsh fabric likely to be very stiff and to have poor handling qualities, especially if one attempts to make up such webs into thick or multilayer fabrics, and this severely limits the usefulness of such material at least in this field of products for surgical and medical purposes.

In carrying out the invention, the treatment step for eliminating or reducing inter-fibre bonding may comprise subjecting the dried sheet or web of the overlaid fibres after the dewatering drying operation to mechanical action which mechanically stresses individual fibres and promotes breakage of any bonds existing therebetween.

Alternatively, or in addition, the treatment may comprise adding a material at an earlier stage of the process which prevents or inhibits the formation of inter-fibre bonding in the de-watering drying operation. Such additive could comprise a substance, such as emulsified oil for example or even a silicone, introduced before the dewatering dyring operation and effective to coat the fibres so as to prevent or inhibit bonding; or it may comprise a water soluble organic solvent, for example a lower alkyl alcohol or acetone, effective to exchange at least a proportion of the water carried by the fibres.

In the latter case, the organic solvent treatment constitutes a stage of the dewatering drying operation and may be useful in any event, in addition to a mechanical treatment, for reducing the amount of water which needs to be removed by other drying means. But, by controlling the nature, amount and manner of application of the organic solvent, for example by using concentrated alcohol in a counter-current arrangement, the quantity of water exchanged and dewatering effect obtained can in some cases be sufficient in itself to prevent the occurrence of any significant degree of inter-fibre bonding in forming the dried non-woven web.

Adding a coating substance such as an emulsified oil may give greater problems in obtaining a final product of acceptable quality, but if this method is used the substance is preferably added to coat the wet spun fibres before laying the sheet thereof onto the moving conveyor.

In preferred embodiments the treatment by mechanical action is employed, preferably by applying mechanical force to the dried sheet or web to pull and tension the overlaid fibres. Such pulling force is preferably applied lengthwise to the fibres by passing the sheet or web through successive sheet feeding means, such as two closely spaced pairs of parallel rollers, the first pair of rollers being driven to provide a feed rate equal to the linear speed of the moving conveyor and the second pair of rollers, which is positioned furthest downstream of the travelling sheet or web, being driven to provide a faster feed rate.

The feed rate of the second pair of such rollers may be matched with approximate equality to the rate at which the sheet of wet spun undried fibres is fed onto the moving conveyor, the action then being merely to break any inter-fibre bonds and provide a dried non-woven web suitable for gathering into a tow for staple cutting. Or, alternatively, the speed of the second pair of rollers may be such as to give a feed rate which is significantly greater, for example at least 20% greater, than the rate of feeding the sheet of wet spun undried fibres onto the moving conveyor whereby a "stretch-breaking" effect is obtained yielding a web material containing randomly broken generally parallel fibres extending lengthwise of the web. The non-woven web produced by this "stretch-breaking" process necessarily has minimal inter-fibre bonding and may be similar in appearance to the output from a textile card; it is generally suitable for the production of a non-woven multilayer wadding by overlaying, preferably by crosslaying, a plurality of layers of such web material.

Thus, according to this further aspect, the invention also provides a process for the production of dried alginate fibre material which includes the operations of spinning an aqueous solution of a soluble alginate salt into a spin bath containing an aqueous solution of a salt, for example a calcium salt, to provide wet spun fibres of insoluble alginate, forming a sheet of the wet spun insoluble undried alginate fibres in which the individual fibres are separated and disposed in generally parallel relationship, feeding forwards and laying the sheet of undried fibres onto a moving conveyor device which is travelling at a slower speed than said sheet in the feed direction whereby the fibres become overlaid in cross-ingover intersecting relationship to form a web, having a defined width. Then the sheet or web of intersecting overlaid fibres is subjected to a dewatering drying operation. After the dewatering drying operation, the sheet or web of overlaid fibres is subjected to a "stretch-breaking" operation to cause said fibres to be randomly broken.

In making up such non-woven wadding for surgical dressings and the like, the layers of the dried web may be subjected to a needling operation or other mechanical action effective to assist in holding the layers together by mechanical interlocking of individual fibres of adjacent layers; or a controlled degree of fibre bonding between the layers may be introduced by spraying either with water (in the case of the web being composed of relatively soluble sodium/calcium mixed salt alginate fibres) or (in the case of the web being composed of insoluble calcium alginate fibres) with an aqueous solution of a salt of an acid which has a water insoluble calcium salt, such as sodium citrate for example, the spray being controlled in quantity in order to control the degree of bonding between the layers. For preference, such spray is applied by means of an airless sprayer.

If staple cut tow is produced, this may be used either to make up a wadding by air laying or to make alginate wool, both being suitable for medical or surgical purposes.

After the initial spinning operation in the spin bath but before being laid on the moving conveyor, the newly spun alginate fibres are preferably also stretched in order to orientate the alginate molecules in the fibres, and this stretching is conveniently performed at an elevated temperature above room temperature by, for example, passing the fibres through a hot water bath.

The sheet of separated and generally parallel undried wet spun alginate fibres can be formed directly by use of a spinning jet having spinning apertures arranged evenly throughout a narrow rectangular area which may extend for the full working width of the spin bath and/or conveyor device. Or, a conventional circular jet may be used for spinning and the wet spun fibres, conveniently gathered into the form of a tow, may be passed through a spreader which spreads them apart evenly in parallel relationship into a substantially uniform thin layer or band for laying onto the moving conveyor. Such a layer or band obviously has a defined width.

In the latter arrangement, it can be advantageous to use a known form of spreader comprising a "fish tail" device in which the wet spun fibres are conveyed by a stream of liquid which proceeds from a narrow but relatively deep cross-section entry slot, through a chamber having a cross-section of substantially constant area throughout its length but of progressively varying shape, to a horizontally extending exit slot of the same or very slightly smaller cross section. Alternatively, the spreader may comprise a mechanical spreader device such as, for example, a cambered roller or series of cambered rollers or a curved bar type spreader. In either case, a web having a defined width is necessarily produced.

In preferred embodiments, the sheet of undried wet spun alginate fibres is fed forwards onto the moving conveyor device at a speed which is at least 20% greater than the speed of travel of the conveyor. Conveniently, the conveyor device is a Fourdrinier mesh conveyor or similar liquid permeable moving belt conveyor.

If it is desired to convert the calcium alginate fibres to the sodium/calcium alginate mixed salt form, this is preferably carried out while the web or sheet is still on the conveyor immediately after the dewatering drying operation carried out on the sheet or web of undried fibres. The conversion is preferably carried out by exchanging a proportion of the calcium ions for sodium ions, this being accomplished by treating the sheet or web with a solution of sodium acetate in aqueous alcohol solution, the concentration of the alcohol being between 10% and 30% by volume, and finally washing with alcohol before further drying. In performing this exchange treatment, the sheet or web of the calcium alginate fibres may advantageously be first treated with a measured quantity of an acidic agent, for example acetic acid, in order to remove calcium ions which are to be replaced, then washed with water and finally exchanged with the aqueous alcoholic solution of sodium acetate to which sodium hydroxide or carbonate or bicarbonate is added to maintain the pH between 5 and 7, preferably between 5.5 and 6.

In some cases, the web or sheet of dried fibres may also be treated so as to exchange a proportion of the metal cations by a cationic radical of an organic base, such as novocaine (procaine) or lignocaine (xylocaine), having analgesic properties.

The controlled treatment step for eliminating or reducing bonding of the overlaid fibres should be such that in the dried non-woven web of the alginate fibre material obtained the tenacity of the web measured in the transverse direction is not more than 25%, and is preferably not more than 10%, of the tenacity measured in the longitudinal direction. Such measurements can be carried out by a standard type of tensile testing instrument.

The actual values of tenacity measured will depend of course not only on the degree of inter-fibre bonding but also on the density of the material in terms of size and number of fibres or filaments. Generally, however, for dried webs of alginate fibre material provided by the present invention the tenacity measured in the longitudinal (machine) direction will be at least 5 g/cm per gram per square meter basis weight (e.g. 300 g/cm for alginate web material of 60 g.s.m.) whereas the tenacity measured in the transverse or cross direction will be not more than 1.25 g/cm for the same basis weight (e.g. 75 g/cm again for material 60 g.s.m.).

BRIEF DESCRIPTION OF THE DRAWING

The accompanying drawing is a diagrammatic representation of apparatus suitable for use in the process.

DESCRIPTION OF PREFERRED EMBODIMENT

By way of example, the carrying out of the process in accordance with the invention will be further described with reference to said drawing.

First, in a spinning machine (not shown) a continuous tow of calcium alginate fibres is produced by spinning an aqueous solution of sodium alginate into an aqueous solution of calcium ions. The fibres are given the necessary mechanical properties by orienting the molecules by stretching as in conventional synthetic fibre spinning, this preliminary stretching being for preference performed at an elevated temperature and for convenience and control this may be achieved by running the tow through a bath of hot water before this stretching stage.

Some method of control of the biodegradation of the spinning solution is also required and this is for preference provided by treatment of the solution with sodium hydrochlorite at a dosage of 1-10% (preferably 3%) available chlorine on sodium alginate. Also, the spinning solution will generally be allowed to stand for a period before spinning in order to deaerate.

Referring now to the drawing, the tow 10 so produced is fed from the spinning machine into a spreader 12 designed to separate all the fibres into a thin sheet of parallel individual fibres. The device consists of a spreader box or tank 14, below a header roll 16, through which water flows from an inlet 18. The tank has at its base an exit 20. This exit 20 is connected to a fish-tail 22, the cross-section of which is substantially constant over its length but which varies from a narrow deep vertical slot of approximately rectangular shape at the entry point to a wide, shallow horizontal slot of approximately rectangular shape at its outlet 24. The word "approximately" is to be taken in this context to mean that the corners may be rounded. Use of a spreader of this form is an alternative to another possible arrangement in which a spinning jet is provided of rectangular shape having its spinning holes spaced evenly within a narrow band extending across the full width of the spin bath and/or the following moving conveyor device.

The spread tow is fed onto a Fourdrinier wire mesh conveyor 26, constituting the moving conveyor device, at an overfeed speed, thus giving a looping or crimping and overlaying of the fibres and destroying their parallel orientation, the fibres then lying in crossing-over intersecting relationship forming a sheet or web 25. The Fourdrinier includes drive rolls 28, 30, and a water drainage receptacle 32.

The sheet or web on the Fourdrinier may then be exchanged with a water soluble organic solvent—preferably alcohol or industrial methylated spirit (I.M.S.)—applied through sprays 34 and collected in troughs 36. Although this stage is not essential in this particular embodiment, the higher the final alcohol level, the less the inter-fibre adhesion and bonding obtained, and the lower the evaporative load on the following evaporative drying devices. An alcohol level of greater than 50% v/v in the final wash is preferred.

The web is then dried in this embodiment by a hot air drier 38 in a recirculatory air system. This arrangement avoids imposing any mechanical forces on the web which would promote fibre-fibre bonding. For the same reason, it will be noted that no suction device is used for removing water, and the web is not passed over pressure rolls before or during drying.

If it is desired to convert the dried web to the more soluble sodium/calcium mixed salt form which is preferred for many uses, the web is next first treated with a measured amount of acetic acid (or HCl) to remove that proportion of calcium ions which will be replaced by sodium ions. Excess acid is removed by washing with water. Then the web is treated with a solution of sodium acetate in a 10-20% v/v I.M.S./water mixture. The acetic acid released is neutralized by addition of NaOH or $Na_2CO_3$ at such a rate that the pH is kept in the range 5.5 to 6.0. This conversion is extremely rapid since it relies on exhange of sodium ions from a fully ionized solution of a sodium salt in concentrations in excess of N/10, rather than neutralization by solutions of hydroxyl ions whose concentration is severely restricted by the necessity to keep the pH below about 9.0. The converted web is finally washed with I.M.S. and then dried with a further hot air drier (not illustrated) as previously described.

If it is not desired to convert to the sodium/calcium mixed salt form so that the web remains composed of insoluble calcium alginate fibres, the above stage is omitted.

In the following stage, the dried web of fibres, shown at 50, is pulled or stretched by passing it through two pairs of parallel rollers 40, 42, whose axes are placed as close to each other as possible, the second pair 42 rotating slightly faster than the first pair 40. If the circumferential speed of the second pair of rollers 42 is the same as the feed rate of the tow through the spreader and fish tail, any bonding at fibre crossover points will be broken, and the result will be a sheet or web of continuous individual filament fibres extending lengthwise of the web. However, if the speed of the second pair of rollers 42 is further increased, the fibres will be stretch-broken in the same manner that happens in conventional break-spinning of textile fibres. The result is then to produce a thin web of fibre material, very similar in appearance to that derived from carding staple fibre. The loops imparted to the fibres by laying on the Fourdrinier as described result in the fibres even after drying being slightly crimped, and this contributes to the unitary web forming properties thereof in the absence of actual inter-fibre bonding.

By arranging for the drive speeds of the rollers to be adjustable during operation to vary the relative feed rates, the degree of "stretch-breaking" produced can be controlled.

In the drawing, the linear speed of the incoming tow 10 to and through the spreader 12 is denoted by $V_1$, that of the Fourdrinier conveyor and the circumferential speed of the first pull rolls 40 is denoted by $V_2$, and the circumferential speed of the second pull rolls 42 is denoted by $V_3$. It follows, therefore, that in carrying out the process in this embodiment $V_1 > V_2$ and $V_3 > V_2$. Also $V_3 \geq V_1$.

The dried alginate fibre material provided by the dried non-woven web of fibres, indicated at 50', derived from the above pulling stage forms the initial end product of the process described but it can then be further processed to make up various preparations especially suitable for medical or surgical use.

Thus, the material can then be made into a wadding, preferably by cross-laying a plurality of layers which, incidentally, will tend to make unimportant any non-uniformity of the web across its width. A controlled degree of bonding between the layers may be introduced by use of a controlled supply of water, applied by an airless sprayer or, preferably, by subjecting the material to a needling operation or other mechanical action effective to interengage fibres of adjacent layers and hold the layers together. Such mechanical action, by its effect in mechanically stressing individual fibres, can also promote breakage of any residual inter-fibre bonding remaining within each individual layer. The resulting wadding is suitable for packing as surgical dressings without further treatment.

In the event that it should be required to produce a wadding from material composed of insoluble calcium alginate fibres rather than of fibres of the more soluble sodium/calcium mixed salt form, instead of using a water spray for achieving interlayer bonding as mentioned above the latter may be substituted by a spray of an aqueous solution of a sodium salt, of which the corresponding calcium salt is insoluble in water, for example sodium citrate.

Should the fibre material be required in a form suitable for wool or for blending with diluent fibres the dried web from the pulling stage may simply be gathered into a tow which can be staple cut. Or, as previously indicated, such staple cut tow can be made up into comparatively thick wadding, by using for example an air laying technique, and if desired other kinds of fibres can be mixed in as a diluent at this stage.

I claim:

1. A process for the production of dried alginate fibre material comprising the steps of:
    (a) spinning an aqueous solution of a soluble alginate salt into a spin bath containing an aqueous solution of a salt, to produce wet spun continuous fibres of insoluble alginate,
    (b) forming a sheet of the wet spun insoluble undried alginate fibres in which the individual fibres are separated and disposed in generally parallel relationship,
    (c) feeding forwards and laying the sheet of undried fibres onto a moving conveyor device which is travelling at a slower speed than said sheet in the feed direction whereby the fibres become overlaid in crossing-over intersecting relationship to form a web configuration having a defined width,
    (d) dewatering the web configuration of intersecting overlaid fibres to effect a drying operation to produce a dried web of crossing-over fibres having a minimal amount of bonding between said fibres,
    (e) said process including treating the fibres of the web to minimize the bonding together of the overlaid crossing-over fibres at their point of contact during the dewatering step, and then following the dewatering step,
    (f) stretch-breaking the sheet of overlaid fibres across the width of the web to to cause said fibres to be disposed generally parallel with respect to each other and extending lengthwise of the web while being randomly broken and to further cause the breaking apart of bonded, crossed-over fibres.

2. A process as defined in claim 1 wherein
the stretch-breaking step includes applying mechanical force to pull and tension the overlaid fibres lengthwise.

3. A process as defined in claim 2 wherein
the mechanical force applying step includes passing the sheet through successive sheet-feeding means driven at different feed rates with respect to each other.

4. A process as defined in claim 3 wherein
the sheet-feeding means is adjustable during operation to vary the relative feed rates and control the degree of random breaking of the fibres.

5. A process as defined in claim 1 wherein
the dewatering drying operation is carried out on the conveyor without direct application to the fibre web of suction, or of heated drying cylinders, or of any other means calculated to subject the fibres to significant mechanical forces effective to promote bonding therebetween.

6. A dried non-woven web of alginate fibres comprising:
(a) dried alginate fibre material as produced in the process of claim 1 wherein the tenacity of said web measured in the transverse direction is not more than twenty-five percent (25%) of the tenacity measured in the longitudinal direction.

7. A dired non-woven web of alginate fibres comprising:
(a) dried alginate fibre material as produced in the process of claim 1 wherein the tenacity of said web measured in the longitudinal (machine) direction is, per gram per square meter basis weight of material, at least 5 g/cm while the tenacity measured in the transverse direction is not more than 1.25 g/cm for the same basis weight.

8. A process for producing a medical preparation useful for surgery, said process comprising the steps of:
(a) producing a dried non-woven web of alginate fibres with a tenacity of said web measured in the transverse direction that is not more than twenty-five percent (25%) of the tenacity measured in the longitudinal direction, and then
(b) forming the material of said web into a tow, then
(c) subjecting said tow to a staple cutting operation, and
(d) making up the staple cut fibres into alginate wool or wadding material suitable for such medical preparation.

9. A process for producing a medical preparation useful for surgery, said process steps comprising:
(a) producing a dried non-woven web of alginate fibres with a tenacity of said web measured in the transverse direction that is not more than twenty-five percent (25%) of the tenacity measured in the longitudinal direction, and then
(b) overlaying a plurality of layers of the material of said web to make up a wadding material suitable for such medical preparation.

10. A process as defined in claim 9 wherein
the layers of said web are cross laid and subjected to mechanical action effective to interengage fibres of adjacent layers and assist in holding the layers together.

11. A process as defined in claim 10 wherein said mechanical action comprises a needling operation.

12. A process as defined in claim 10 wherein
the mechanical action is effective to mechanically stress individual fibres thereby promoting breakage of any residual inter-fibre bonding remaining within each individual layer.

13. A process as defined in claim 9 wherein
a controlled degree of bonding between the layers is introduced by spraying the web with a controlled quantity of water when said web is composed of relatively soluble sodium/calcium mixed salt alginate fibres.

14. A process as defined in claim 9 wherein
a controlled degree of bonding between the layers is introduced by spraying the web with a controlled quantity of an aqueous solution of a soluble salt of an acid having a water insoluble calcium salt when said web is composed of insoluble calcium alginate fibres.

15. A process as defined in claim 2 wherein
the mechanical force is applied over the entire width of the sheet-like web to produce a thin web of fibre material resembling material derived from carding staple fibre.

16. A process as defined in claim 15 wherein
the mechanical force applying step includes passing the sheet-like web through successive sheet-feeding means driven to provide different feed rates.

17. A process as defined in claim 16 wherein
the sheet-feeding means is adjustable during operation to vary the relative feed rates and control the degree of random breaking of the fibres.

18. A process as defined in claim 16 wherein
the sheet-feeding means disposed furthest downstream of the travelling sheet-like web, which means provides the faster feed rate, is driven so that said faster feed rate is at least twenty percent (20%) greater than the rate at which the sheet of wet spun undried fibres is fed onto the moving conveyor as to effect the stretch breaking step.

19. A process as defined in claim 1 wherein
the minimal bonding treating step includes applying a water soluble organic solvent to the web of undried overlaid fibres while on the moving conveyor to exchange at least a proportion of the water carried by said fibres,
this solvent applying treatment constituting a stage of the dewatering drying operation.

20. A process as defined in claim 19 wherein
said organic solvent comprises a lower alkyl alcohol or acetone.

21. A process as defined in claim 19 wherein
the nature, amount and manner of application of the organic solvent is controlled so that the quantity of water exchanged and dewatering effect obtained is sufficient in itself to prevent the occurrence during drying of the fibres in the web of any significant degree of inter-fibre bonding of the overlaid fibres at their points of contact or intersection.

22. A process as defined in claim 21 wherein
the treatment with the water soluble organic solvent is carried out in a counter-current exchange arrangement.

23. A process as defined in claim 1 wherein
the minimal bonding treating step includes coating the wet spun undried fibres prior to the dewatering drying operation with a substance effective to inhibit inter-fibre bonding and to prevent the occurrence of any significant degree of such bonding at the points of contact or intersection of the overlaid fibres during the subsequent dewatering drying operation.

24. A process as defined in claim 23 wherein the coating substance is an oil applied as an additive in emulsified form to the wet spun fibres before laying the sheet of the latter onto the moving conveyor.

25. A process as defined in claim 1 wherein the dewatering drying operation is carried out on the conveyor without direct application to the fibre web of suction, or of heated drying cylinders, or of any other means calculated to subject the fibres to significant mechanical forces effectove to promote bonding therebetween.

26. A process as defined in claim 1 wherein the sheet forming step includes passing a tow of the wet spun fibres through a spreader which spreads them apart evenly onto a substantially uniform thin layer or band for laying onto the moving conveyor.

27. A process as defined in claim 26 wherein the spreader comprises a "fish tail" device in which the wet spun fibres are conveyed by a stream of liquid through a chamber having a cross-section of substantially constant area throughout its length but of progressively varying shape from a vertically extending entrance slot to a horizontally extending exit slot.

28. A process as defined in claim 1 wherein the sheet forming step includes stretching the wet spun alginate fibres after the spin bath but before being laid on the conveyor thereby to orient the alginate molecules in the fibres.

29. A process as defined in claim 28 wherein the said wet spun fibre stretching step is performed at a temperature elevated above ambient room temperature.

30. A process as defined in claim 29 wherein the said wet spun fibre stretching step includes passing the fibres through a hot water bath.

31. A process as defined in claim 1 wherein the sheet forming step includes using a spinning jet having spinning apertures arranged evenly throughout a narrow rectangular area.

32. A process as defined in claim 1 wherein the sheet of undried wet spun alginate fibres is fed forwards onto the moving conveyor device at a speed which is at least twenty percent (20%) greater than the speed of travel of said conveyor.

33. A process as defined in claim 1 wherein the moving conveyor device is a liquid permeable conveyor comprising a Fourdrinier mesh conveyor.

34. A process as defined in claim 1 wherein after the dewatering operation which is carried out on the web of undried overlaid wet spun fibres on the conveyor device, the resulting web of dried fibres is treated so as to exchange a proportion of the cations forming the insoluble alginate fibres for alkali metal cations thereby to covert the fibres into a more soluble mixed alginate salt form.

35. A process as defined in claim 34 wherein the cation exchange and conversion step is carried out by treating the web of dried fibres with a solution of sodium acetate in aqueous alcohol.

36. A process as defined in claim 35 wherein the web of dried fibres is first treated with a measured quantity of an acidic agent before the treatment with the sodium acetate solution while maintaining the pH between 5 and 7 during said latter treatment.

37. A process as defined in claim 34 wherein the stretch-breaking step is effected after carrying out said cation exchange and conversion step.

38. A process as defined in claim 1 wherein the web of dried fibres is treated to exchange a proportion of the cations by a cationic radical of an organic base having analgesic properties.

39. A process as defined in claim 38 wherein the organic base comprises novocaine or lignocaine.

40. A unitary, dried non-woven web of alginate fibres comprising:
    (a) fibres disposed generally parallel with respect to each other and extending lengthwise of the web,
    (b) there is a minimal inter-fibre bonding with the fibres being randomly broken along their lengths,
    (c) The tenacity of said web has a value when measured in the transverse direction which is not more than twenty-five percent (25%) of the tenacity measured in the longitudinal direction.

41. A unitary, non-woven web as defined in claim 40 wherein the tenacity in the transverse direction is not more than ten percent (10%) of the tenacity in the longitudinal direction.

42. A unitary, dried non-woven web of alginate fibres comprising:
    (a) fibres disposed generally parallel with respect to each other and extending lengthwise of the web,
    (b) there is a minimal inter-fibre bonding with the fibres being randomly broken along their lengths,
    (c) the tenacity of the web measured in the longitudinal (machine) direction is, per gram per square meter basis weight of material, at least 5 g/cm while the tenacity measured in the transverse direction is not more than 1.25 g/cm for the same basis weight.

* * * * *